United States Patent [19]
Ismail

[11] Patent Number: 5,578,499
[45] Date of Patent: Nov. 26, 1996

[54] HOMOGENEOUS IMMUNOASSAY SYSTEM EMPLOYING FOURIER TRANSFORM INFRARED SPECTROSCOPY

[75] Inventor: Ashraf A. Ismail, Westmount, Canada

[73] Assignee: The Royal Institution for the Advancement of Learning, Montreal, Canada

[21] Appl. No.: 231,977

[22] Filed: Apr. 21, 1994

Related U.S. Application Data

[63] Continuation of Ser. No. 875,802, Apr. 30, 1992, abandoned, which is a continuation-in-part of Ser. No. 409,788, Sep. 20, 1989, abandoned.

[51] Int. Cl.$^6$ .................. G01N 33/551; G01N 33/552
[52] U.S. Cl. .............. 436/524; 250/227.19; 250/227.23; 250/227.27; 250/340; 356/51; 356/317; 356/318; 356/346; 356/244; 422/82.05; 422/82.09; 422/82.11; 435/808; 435/973; 436/164; 436/527; 436/528; 436/531; 436/532; 436/536; 436/537; 436/805
[58] Field of Search ................ 250/227.14, 227.19, 250/227.23, 227.27, 338.1, 338.5, 339, 340, 341, 343; 356/51, 317, 318, 356, 343, 346, 463, 244, 246; 422/82.05, 82.09, 82.11; 435/808, 973; 436/164, 518, 527, 528, 531, 532, 536–538, 805, 524

[56] References Cited

U.S. PATENT DOCUMENTS

| | | | |
|---|---|---|---|
| Re. 33,064 | 9/1989 | Carter et al. | 436/34 |
| 4,880,752 | 11/1989 | Keck et al. | 435/7 |
| 4,975,581 | 12/1990 | Robinson et al. | 250/339 |
| 5,120,131 | 6/1992 | Lukosz | 356/345 |
| 5,218,419 | 6/1993 | Lipson et al. | 250/227.14 |
| 5,422,283 | 6/1995 | Ismail | 436/525 |

OTHER PUBLICATIONS

Ismail et al; Clin Chem, 33(6) Jun. 1987 Abstract #216.
Ismail et al., Clin Biochem 22(4) 297–299 Aug. 1989.
Baugs, From Uniform Latex Particles, Seradyn Inc pp. 47–50, 58.
Boiarski et al., SPIE, vol. 1368 (1990) pp. 264–272.
Janatsch et al., Anal Chem 1989 (Sep. 15), 61, 2016–2023.
Pidgeon et al., Analyt Biochem 181, 28–32 (Aug. 15, 1989).

*Primary Examiner*—James C. Housel
*Assistant Examiner*—Christopher L. Chin
*Attorney, Agent, or Firm*—Cushman Darby & Cushman

[57] ABSTRACT

The present invention relates to an homogeneous immunoassay system for the determination of an antibody or an antigen in a sample which consists of an interferometric signal emitted from an infrared source, a waveguide coated with an antibody or an antigen and having at least one region immersed in an aqueous sample, whereby the corresponding antigen or antibody can be complexed on the surface of the waveguide, a detector adapted to measure the interferometric signal after its propagation through the waveguide, and a measuring device to take the Fourier transform of the interferometric signal for determining the degree of attenuation of the interferometric signal at a wavelength corresponding to an absorption characteristic of an infrared label incorporated into the antigen-antibody complex, whereby determining the concentration of antigen or antibody in the sample.

15 Claims, 10 Drawing Sheets

5,578,499

HOMOGENEOUS IMMUNOASSAY SYSTEM EMPLOYING FOURIER TRANSFORM INFRARED SPECTROSCOPY

This is a continuation of application Ser. No. 07/875,802, filed on Apr. 30, 1992, which was abandoned upon the filing hereof, which was a continuation-in-part of Ser. No. 07/409,788 filed Sep. 20, 1989 now abandoned.

BACKGROUND OF THE INVENTION

Conventional optical spectrometers, such as infrared spectrometers, are dispersive instruments, employing a prism or a grating to separate the radiation emitted by the source into its component wavelengths, with each resulting spectral element detected individually. As a result, these spectrometers are inefficient in their use of the energy available from the source since, at any given time, only a small fraction of the energy reaches the detector. This inefficiency is particularly disadvantageous in applications which involve low energy throughput, such as attenuated total reflectance (ATR) experiments. Conventional spectrophotometers utilize filters to block all wavelengths except the wavelength band of choice and, accordingly, also utilize only a fraction of the source energy.

A Fourier transform infrared (FTIR) spectrometer operates on a totally different optical principle of interferometry. An interferometrically coded signal contains information for a range of wavelengths; computing the Fourier transform of the signal yields a spectrum. The first interferometer was built by Michelson in 1891, and his design is incorporated in most commercial FTIR spectrometers currently in use. A corner cube interferometer is also utilized in some commercial FTIR spectrometers.

The most important factor, in practice, contributing to the sensitivity of Fourier transform optical spectrometry (FTOS), which includes FTIR spectrometry, is Fellgett's advantage, or the multiplex advantage, which gives rise to improvements in signal-to-noise ratio (S/N) and reduction in measurement time for FT spectral acquisition, compared to the time required to obtain spectra with a grating instrument. Fellgett's advantage originates in the fact that information for all wavelengths emitted from the source reaches the detector at the same time in FT measurements, whereas in a grating instrument each spectral element ($vcm^{-1}$, corresponding to the resolution) is detected separately. This results in a dramatic decrease in measurement time if information from a large spectral region is required. This is an important consideration if multiple components absorbing in different regions of the spectrum are to be detected.

Another advantage associated with FTIR spectrometers is Jacquinot's advantage. The magnitude of Jacquinot's advantage is assessed by comparison of the maximum optical throughput permissible before loss of resolution is incurred for a grating spectrometer and an interferometer. In a grating instrument the throughput is significantly limited by the size of the slits, resulting in low throughput. Since there are no slits in an interferometer, more energy impinges on the detector.

The use of a laser in an interferometer to trigger digitization of the signal gives rise to a third advantage, known as Connes' advantage. This refers to the precision (0.003–0.006 $cm^{-1}$) with which frequencies can be determined in FTIR work, because the laser serves as an internal wavelength calibration standard. Since the digitized spectra are stored as a series of data points corresponding to fractions of laser wavelength (which does not vary with time), spectra recorded at widely separated times can be compared with precision. This is a particularly important advantage for data handling techniques such as spectral substraction and coaddition of scans, which can be subject to difficulties when performed on a computerized grating instrument due to drifts in frequency with time.

FTIR spectrometers have been found to be very useful in attenuated total reflectance (ATR) experiments, wherein light from the source is transmitted down a suitable waveguide (the internal reflection element, or IRE), in such a manner that it is totally reflected at the IRE-sample interface, giving rise to an evanescent wave which penetrates into the sample. As a result of the attenuation of the evanescent wave by the sample, the light exiting the IRE and striking the detector is attenuated at wavelengths corresponding to absorptions of the sample, thus yielding the spectrum of the sample. Due to the shallow depth of penetration of the evanescent wave into the sample, a short effective pathlength is obtained. However, the use of ATR techniques with conventional spectrometers is limited by the poor signal-to-noise ratio of the spectra obtained. As a result of the advantages of FT spectrometers, as outlined above, the coupling of ATR techniques with FTIR has made possible the acquisition of high-quality spectra. Several manufacturers have designed small ATR cells offering automatic sampling and self-cleaning capabilities, facilitating the routine quantitative analysis of samples.

RE 33064 (Carter et al.) discloses a method for the determination of an analyte in solution by its reaction with an appropriate reactant coated on the surface of an optical waveguide. The basis of the method is the detection of the modification of a multiply totally reflected light wave travelling through the waveguide core by the formation of a layer of the analyte-reactant product on the waveguide surface. The application of this technique in immunoassay, i.e., the case in which the analyte is an antigen and the reactant is an antibody, or the reverse condition, is included in the teachings of this patent.

It would be highly desirable if to design a system wherein an interferometrically coded signal from an infrared source would be propagated down an optical waveguide, and the resulting attenuation of the evanescent wave would provide a measure of the amounts of an antigen-antibody complex bound on the outer surface of the waveguide.

SUMMARY OF THE INVENTION

In accordance with the present invention, there is provided an homogeneous immunoassay system for the determination of the concentration of an antibody or an antigen in a sample which comprises:

an interferometric signal emitted from an infrared source;

a waveguide coated with an antibody or an antigen and having at least one region immersed in an assay medium consisting of an aqueous sample, whereby the corresponding antigen or antibody can be complexed on the surface of the waveguide;

a detector adapted to measure the interferometric signal after its propagation through the waveguide; and a measuring device adapted to take the Fourier transform of the interferometric signal for determining the degree of attenuation of the interferometric signal at a wavelength corresponding to an absorption characteristic of a label incorporated into the antigen-antibody complex, whereby the concentration of antigen or antibody in the aqueous sample is determined.

Such an homogeneous immunoassay system can be utilized for the determination of the concentration of any antigen or antibody.

The homogeneous immunoassay system of the present invention can also be utilized for the simultaneous determination of multiple analytes in a single homogeneous immunoassay test.

Although the present invention has been described in the foregoing description by way of preferred embodiments thereof, it should be pointed out that it can be modified at will, within the nature of the present invention.

IN THE DRAWINGS

Figure 8:
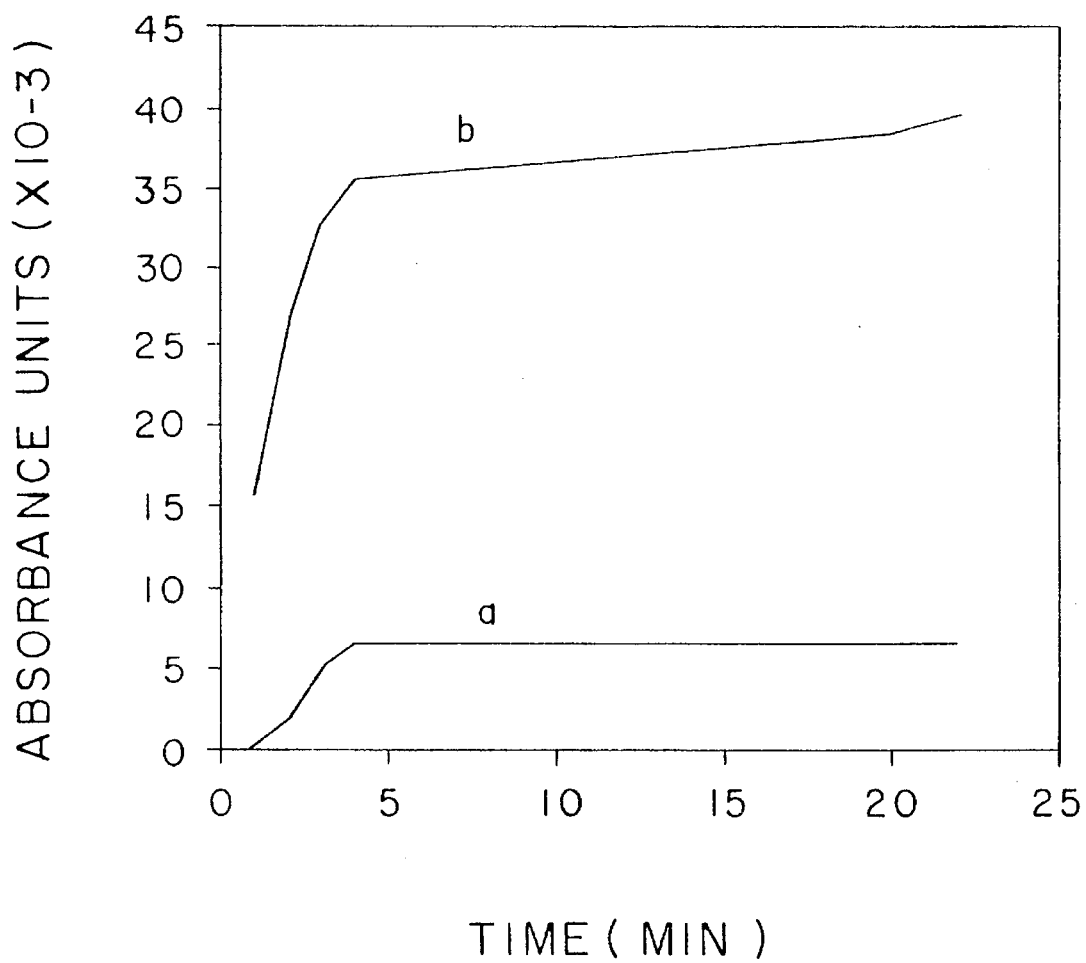
Figure 9:
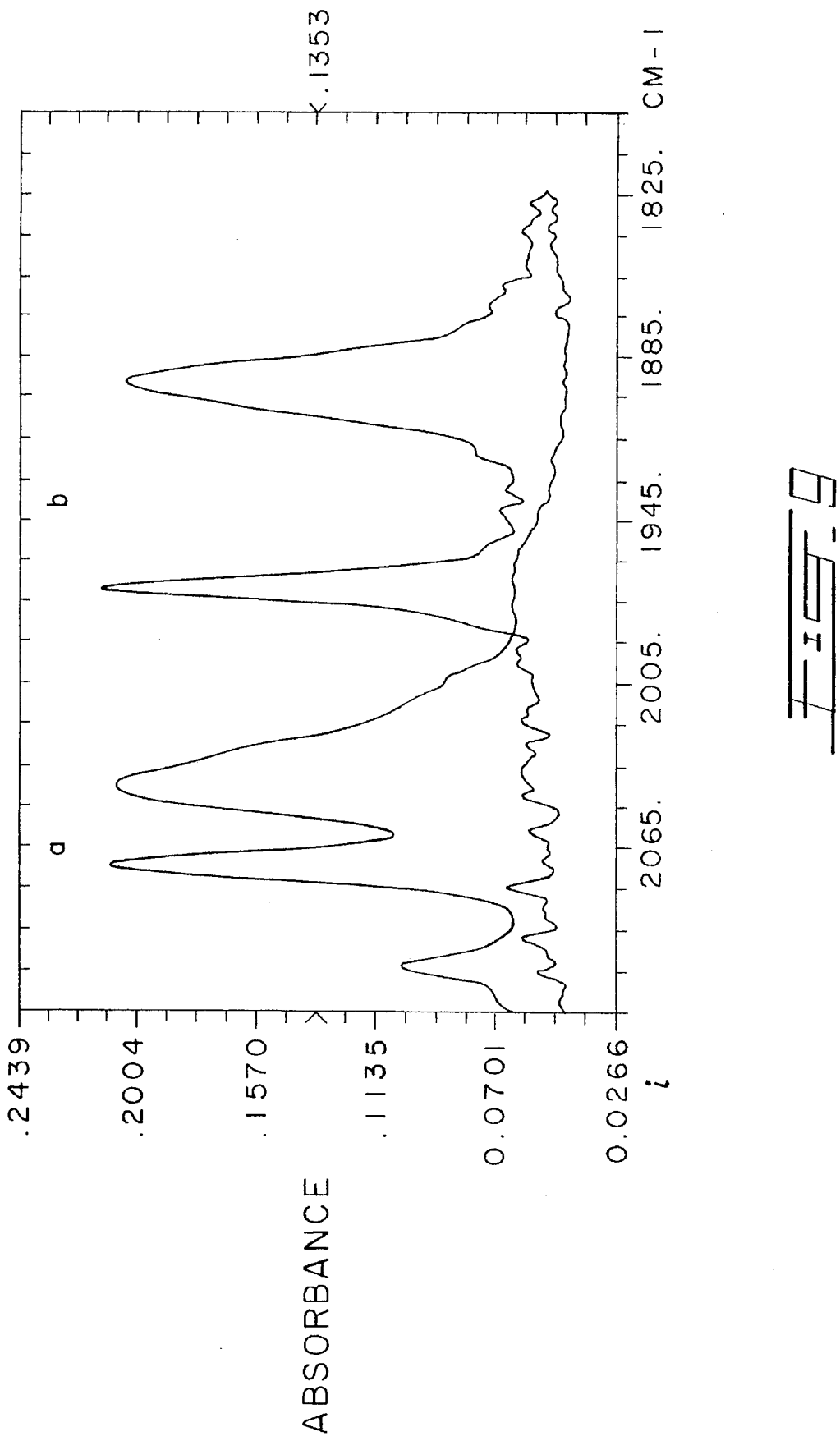

FIG. 8 shows 2 curves representing intensities of the $\nu$(CO) absorptions of the X(CO)$_3$ label in the ATR spectrum measured from the surface of a waveguide immersed in an aqueous sample containing anti-BSA-X(CO)$_3$ (0.3 mg/ml), (a) with a bare waveguide and (b) with a BSA/CML coated waveguide; and FIG. 9 shows superimposition of ATR spectra recorded from the surface of a waveguide coated with (a) BSA-Z(CO)$_6$ and (b) BSA-X(CO)$_3$.

Figure 10:
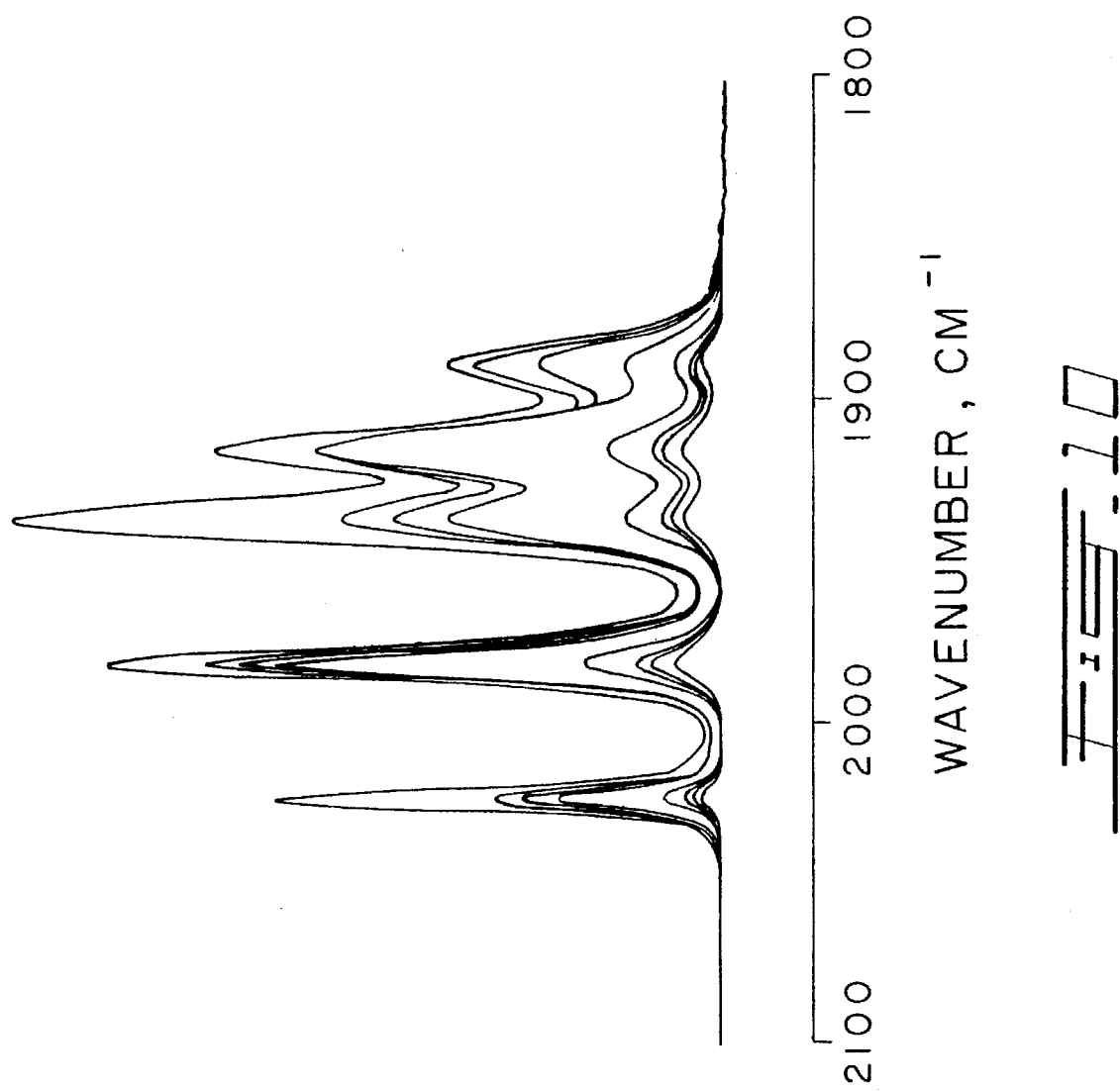

FIG. 10 shows the superimposition of the FTIR spectra in the 2100–1800 cm$^{-1}$ region of 8 toluene solutions containing randomly varying concentrations of three infrared markers.

Figure 11:
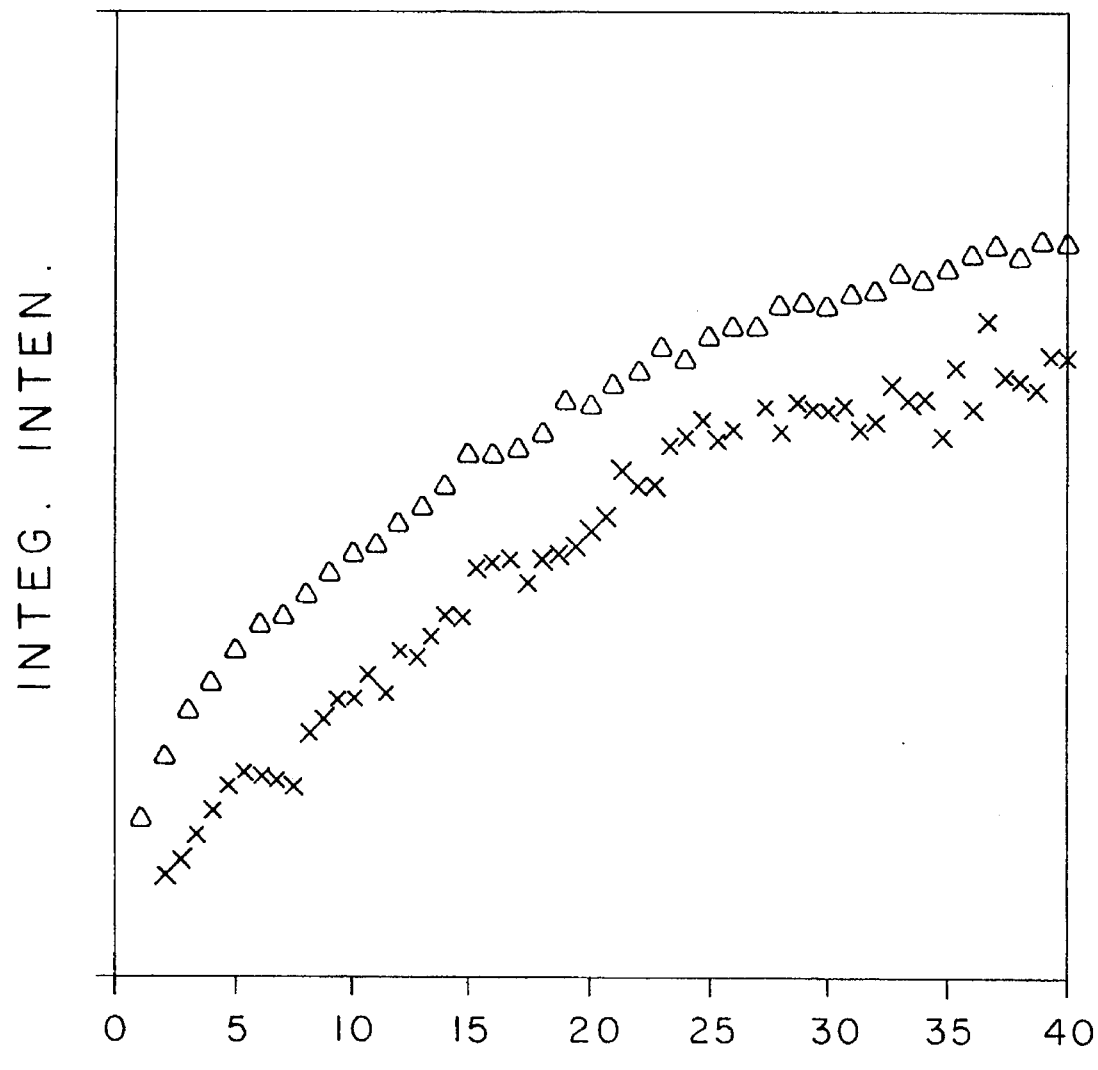

FIG. 11 shows 2 curves reprenting integrated intensities of the $\nu$(CO) absorptions of L-X(CO)$_3$ (1975–1970 cm$^{-1}$;$\Delta$) and L-Y(CO)$_3$ (2022–2018 cm$^{-1}$;x) markers embedded in latex particles bound to anti-tobramycin and anti-gentamicin, respectively, as a function of time after application of a solution containing these labeled antibodies onto an optical waveguide coated with the corresponding antigens.

DETAILED DESCRIPTION OF THE INVENTION

The present invention relates to an immunoassay method in which FTIR spectroscopy is used for the determination of the concentration of an analyte, such as an antigen or an antibody, in an aqueous sample by the measurement of the attenuation of an interferometrically coded infrared signal travelling through an optical waveguide core having suitable infrared transmission properties, the waveguide being in intimate contact with the aqueous sample. The optical waveguide is coated with the reactant and a known amount of the analyte in labelled form is present in the sample containing the analyte to be measured. The attenuation of the interferometrically coded infrared signal results from the absorption of infrared radiation by the label in the analyte-reactant complex formed on the surface of the waveguide. The major advantage of the use of interferometry is that all wavelengths emitted by the infrared source are passed simultaneously through the waveguide and are detected simultaneously by a single detector. This multiplexing advantage is unique to interferometric measurements and allows concurrent evaluation at multiple wavelengths using a single source and a single detector. The labels used in the present invention are molecules or moieties possessing particular infrared absorption characteristics. The detection of the attenuation of the interferometrically coded infrared signal by absorption is employed to determine the concentration of a given analyte in an aqueous sample. The narrow band widths of infrared absorption bands permit the quantitation of multiple species present in one sample from the FTIR spectrum of the sample.

As examples of waveguides suitable for the purposes of the present invention, there may be mentioned a rod, an optical fiber, a slide and the like. Preferably, the rod and the slide are made of zinc selenide, germanium, AMTIR (Ge$_{33}$As$_{12}$Se$_{55}$) (sold by Wilmad), silicon, zirconium fluoride or any other suitable infrared transmitting material of appropriate refractive index for multiple internal refraction. As for the optical fiber, it can be made of zirconium fluoride, a chalcogenide or any other suitable infrared transmitting material of appropriate refractive index for multiple internal refraction. A zinc selenide rod is the most preferred waveguide.

Figure 2:
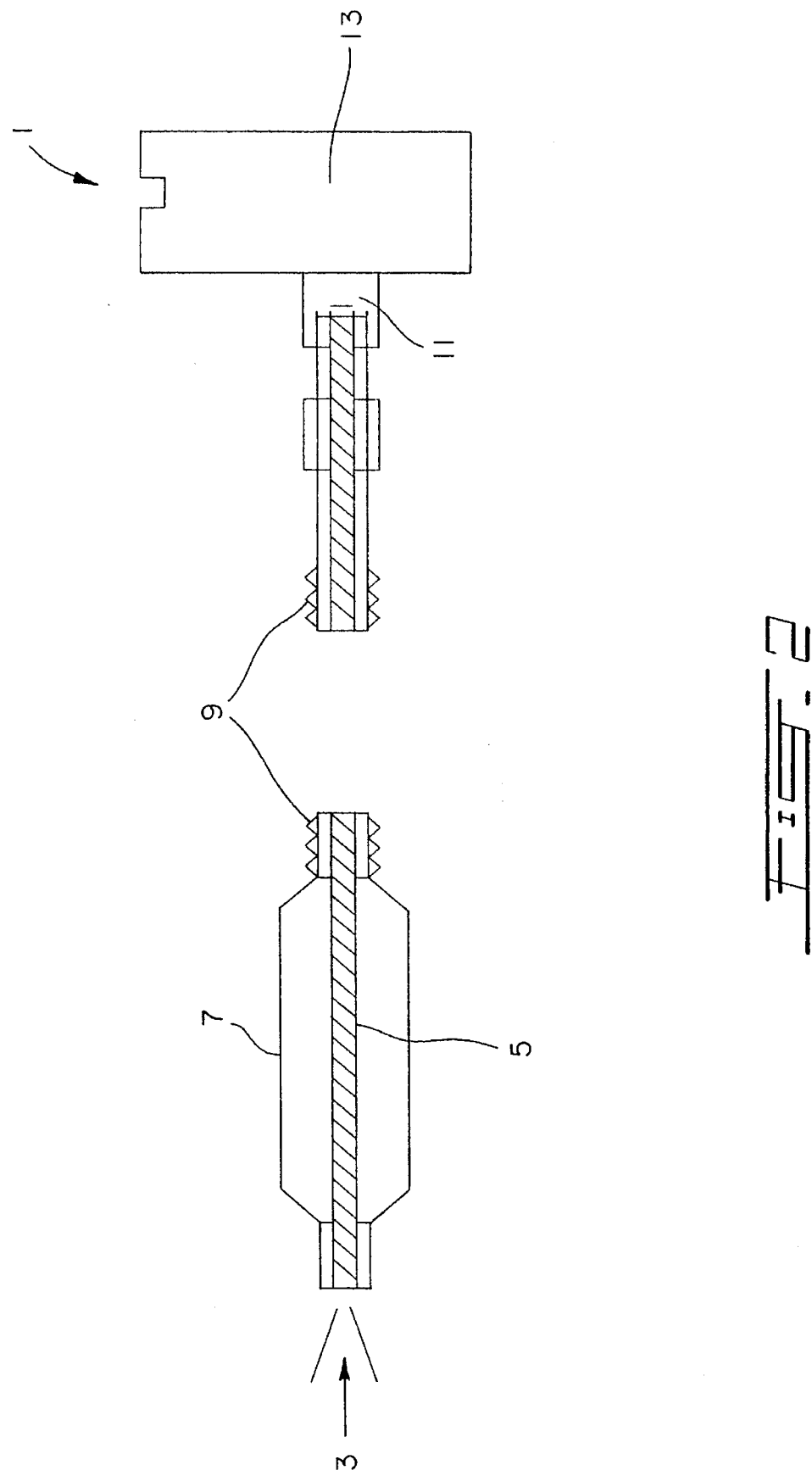
FIG. 2 shows a schematic representation of the homogeneous immunoassay system made in accordance with the present invention.

An embodiment of the homogeneous immunoassay system according to the present invention is shown in FIG. 2 and is generally denoted 1. It mainly consists in coupling of an optical fibre waveguide-based measurement cell to an optoelectronic detector assembly in which there are: a lens or beam condenser 3, an optical fibre waveguide 5, an aluminum sample boat 7, a stainless steel optical fibre coupler 9, a detector element 11, and a detector housing 13.

The use of a beam condenser 3 to focus the interferometric signal onto the waveguide 5 aids in increasing the throughput of the signal reaching the detector 11. A variety of beam condensers are commercially available, and simple lens systems can be assembled. Also a detector design based on optical fibre technology has been implemented to enhance signal detection from optical fiber waveguides.

Figure 1:
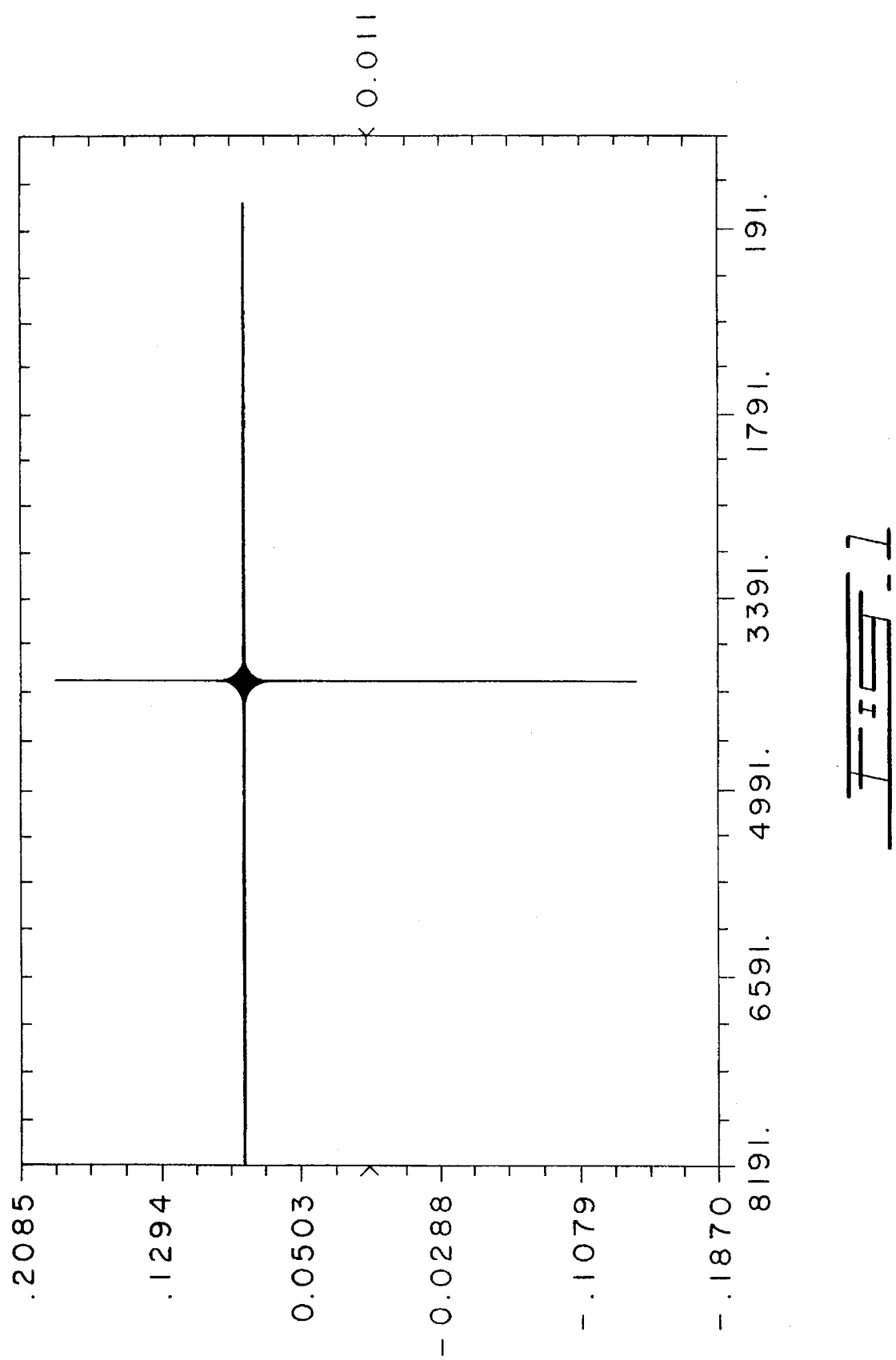
FIG. 1 shows an interferometrically coded signal.

The homogeneous immunoassay system of the present invention is an immunoassay where no separation step is required. In this assay, an optical waveguide coated with an antigen (or antibody) is immersed in an aqueous sample containing the corresponding antibody (or antigen). Introduction of the interferometrically coded signal (FIG. 1) to the waveguide at such an angle that it is internally reflected through the waveguide establishes an evanescent wave at the waveguide-solution interface. The evanescent wave at the waveguide-solution interface has a depth of penetration proportional to the wavelength of the radiation propagating through the waveguide:

$$d_p = \lambda / \{2x[\sin 2\theta - (n_{21})^2]\}0.5$$

where $d_p$ is the depth of penetration, $\theta$ is the angle of incidence, $\lambda$ is the wavelength of light propagating down the waveguide, and $n_{21}=n_2/n_1$, where $n_1$ is the refractive index of the waveguide and $n_2$ is the refractive index of the waveguide and $n_2$ is the refractive index of the medium in contact with the waveguide. The evanescent wave is attenuated by absorption of energy by species present within the volume swept out by the depth of penetration.

In order to bind the antigen or antibody on the surface of the waveguide, the waveguide is coated with a cladding on which the antigen or antibody can be either adsorbed or covalently bound. The thickness of the cladding on the waveguide can be adjusted so that the depth of penetration is sufficient to sample only the antibody-antigen complex (referred to as the "bound" fraction) on the surface of the cladding with very minimal attenuation of the evanescent wave by the uncomplexed antigen or antibody present in solution (referred to as the "free" fraction).

Coating the waveguide with a cladding having a thickness less than the depth of penetration, composed of a solid support onto which an antigen or antibody can be adsorbed or covalently linked, can be accomplished by a variety of methods. In this invention, the coating of a polymer onto the waveguide to serve as the cladding is carried out by an immersion method, the thickness of the film being controlled by the concentration of the polymer in the solution in which the waveguide is immersed. The polymer employed is preferably a carboxy-modified latex polymer. The thickness of the cladding is estimated from the intensities of the infrared peaks due to absorptions of the polymer film. The antigen or antibody can be adsorbed on the polymer film, or covalently linked to the polymer through the carboxyl function. Other methods of thin film deposition can also be utilized to coat the waveguide with an antigen or antibody.

Figure 3:
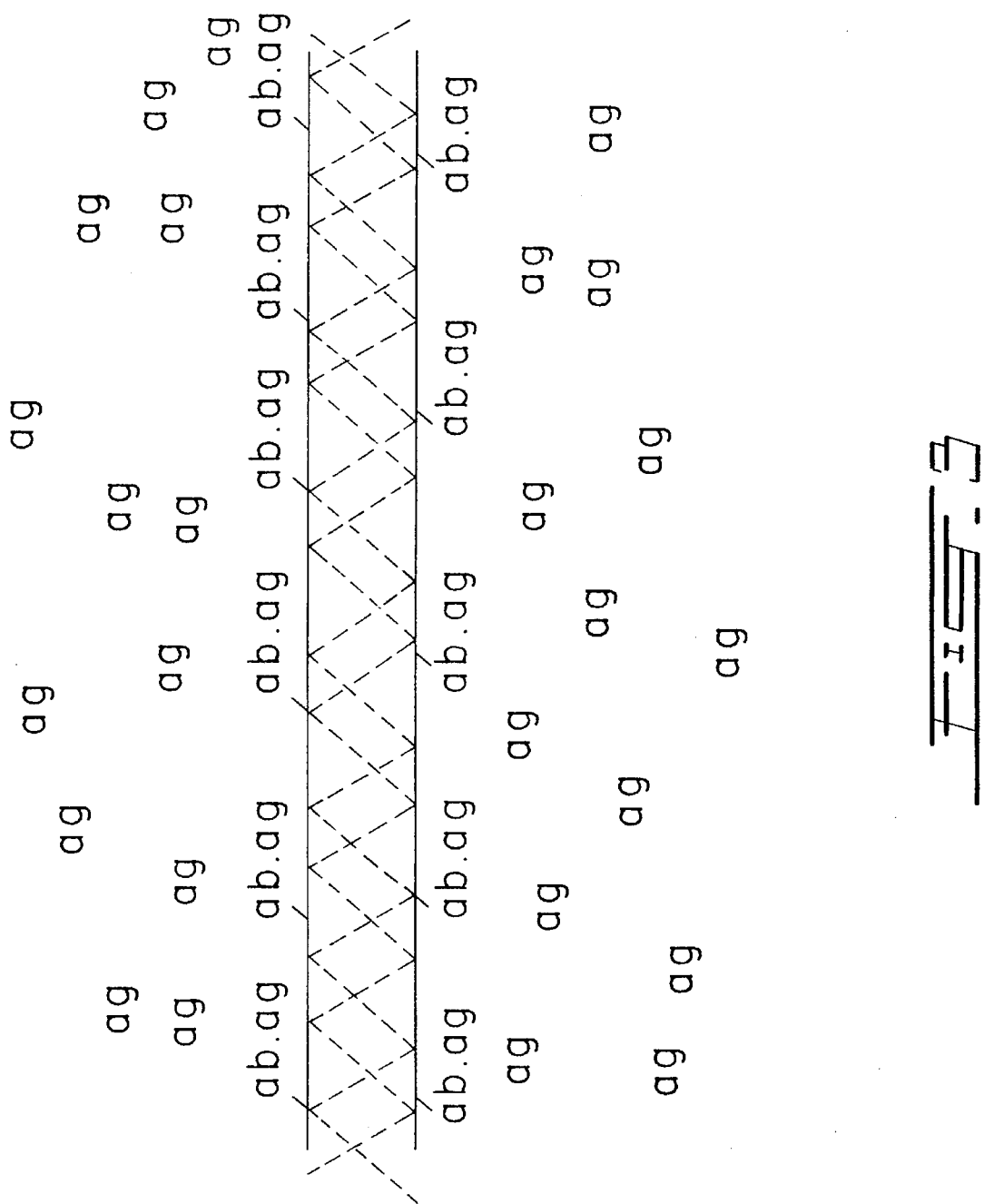
FIG. 3 shows a schematic representation of binding of antigen (ag) present in the aqueous sample to their specific antibodies (ab) immobilized on the surface of a waveguide.

The underlying principle of immunoassay is that the concentration of the antigen-antibody complex is proportional to the concentration of free antigen and free antibody present in the assay medium. Thus, a calibration curve for the determination of an antigen or antibody can be constructed by measuring the concentration of antigen-antibody complex formed upon addition of various known concentrations of antigen or antibody to a solution containing a known concentration of antibody or antigen. It is common practice in immunoassay to use a labelled form of the analyte, which can be readily detected by some appropriate method, competing with the unlabelled analyte for the antibody binding sites to enhance the sensitivity of the assay. In terms of the present invention, the antigen-antibody complex is formed at the surface of the waveguide (FIG. 3), and thus the amount of complex formed is determined by measuring the attenuation of the evanescent wave, which can be monitored as a function of time, or determined at an end point. The attenuation of the evanescent wave is measured at a wavelength corresponding to a characteristic infrared absorption of a marker labelling the antigen or the antibody. Organometallic molecules having characteristic absorptions in the mid-infrared frequency range were obviously preferred as labels in the demonstration of the general viability of the homogeneous interferometric immunoassay of the present invention. Several different types of homogeneous interferometric immunoassay protocols are possible using the present homogeneous immunoassay system.

Figure 4:
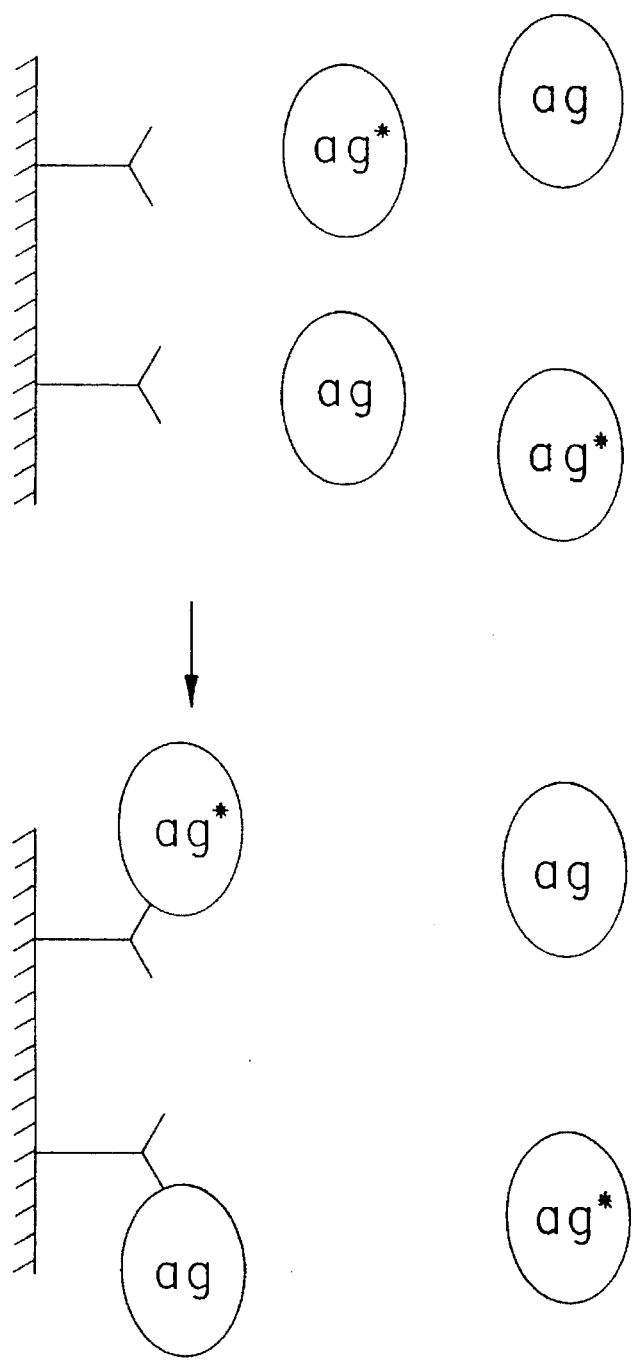
FIG. 4 shows a homogeneous immunoassay system for detecting antigen (ag) according to the present invention in which antibodies are bound onto the waveguide, and a known concentration of labelled antigen (ag*) in the sample competes for the antibody binding sites with the unlabelled antigen (ag)

An homogeneous interferometric immunoassay system for the detection of an antigen (ag) has the antibodies bound onto the surface of the waveguide, and a known concentration of labelled antigen (ag*) in the assay medium competes for the antibody binding sites with the unlabelled antigen (FIG. 4).

Figure 5:
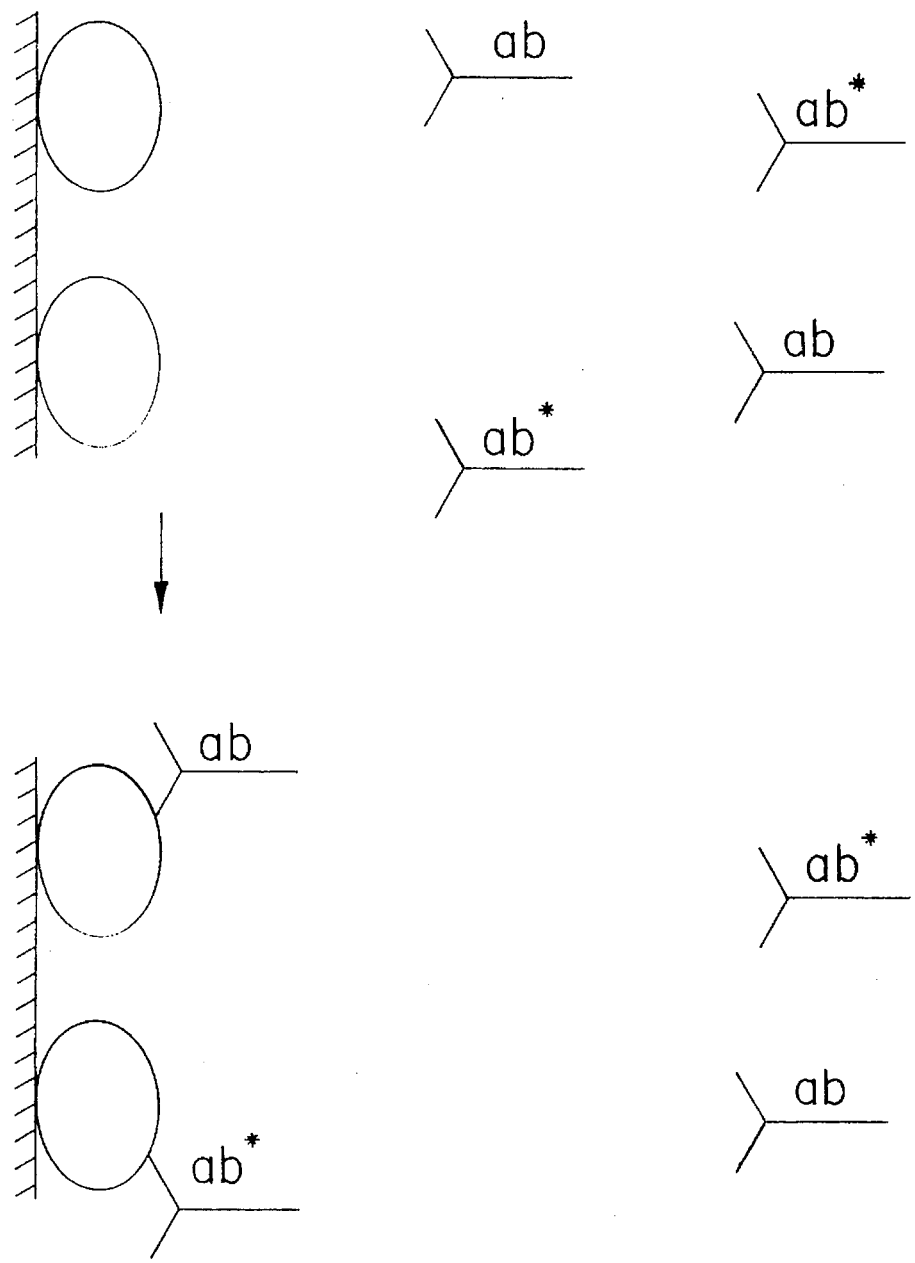
FIG. 5 shows a homogeneous immunoassay system according to the present invention for the detection of an antibody (ab) in which antigens are bound onto the waveguide, and a known concentration of labelled antibodies (ab*) competes for the antigen with the unlabelled antibody.

An homogeneous interferometric immunoassay system for the detection of an antibody (ab) has the antigen molecules bound onto the surface of the waveguide and a known concentration of labelled antibody (ab*) in the assay medium competes for the antigen with the unlabelled antibody (FIG. 5).

An homogeneous interferometric immunoassay system for the detection of an antibody (ab) has antibodies of the same type as the antibodies to be assayed bound onto the surface of the waveguide and competing with the antibodies in the assay medium for labelled antigen molecules also present in the assay medium.

A sandwich-type homogeneous interferometric immunoassay for total antibody content is also possible using the system of the present invention. Antigens are bound onto the surface of the waveguide, and antibodies specific to these antigens are introduced in the assay medium. Following an appropriate incubation period, the assay medium is replaced with a solution containing labelled protein A molecules. Protein A is a substance that binds to the Fc fragment of antibodies. Accordingly, the concentration of labelled protein A bound on the surface of the waveguide allows a measure of the total antibody content of the initial assay medium.

The homogeneous immunoassay system of the present invention can also use the multiplexing advantage of the interferometrically coded signal to detect multiple antigens in a single homogeneous test. Because the interferometrically coded signal covers a wide spectral region, multiple antibodies or antigens having distinct characteristic absorptions can be detected simultaneously. These multiple antibodies or antigens can be coated on the waveguide by several methods. The coating of individual sides of a square waveguide is accomplished by reaction of each side with only one type of antibody or antigen. In this manner, different immunoassays can be performed on the same waveguide. Alternate methods of introduction of multiple antibodies or antigens include serial coating of the antibodies or antigens or the use of optical fiber bundles, with each optical fiber coated with a different antibody or antigen of interest.

The present invention will be more readily understood by referring to the following examples which are given to illustrate the invention rather than to limit its scope.

EXAMPLE I

Homogeneous Interferometric Immunoassay
Without the Use of a Label

The waveguide utilized was a ZnSe rod (8×0.5×0.5 cm) transmitting radiation in the mid-infrared, corresponding to a frequency range between 5000 and 650 cm$^{-1}$. The waveguide was coated with a thin layer (50–3000 nm) of a carboxy-modified latex film, either through immersion of the waveguide in a 5–30% (w/v) carboxy-modified latex (CML) paint (from the Seradyn Corporation) or through the evaporation of an aliquot (50–200 µl) of the CML paint applied to the waveguide. After deposition of the CML layer, the coated waveguide was washed 3 times with distilled water and then immersed in 4 ml of a phosphate buffer (0.01M, pH 7.4) solution containing bovine serum albumin (BSA) (1 mg/ml) and water-soluble carbodiimide [WSC; 1-(3-Dimethylaminopropyl)-3-ethylcarbodiimide hydrochloride] (1 mg/ml). The waveguide was then washed again 3 times with distilled water and 3 times with buffer. An ATR spectrum was recorded from the surface of the waveguide.

The presence of the amide I (1650 cm$^{-1}$) and amide II (1540 cm$^{-1}$) bands of BSA in the spectrum confirms that BSA is bound to the CML coating on the waveguide.

Figure 6:
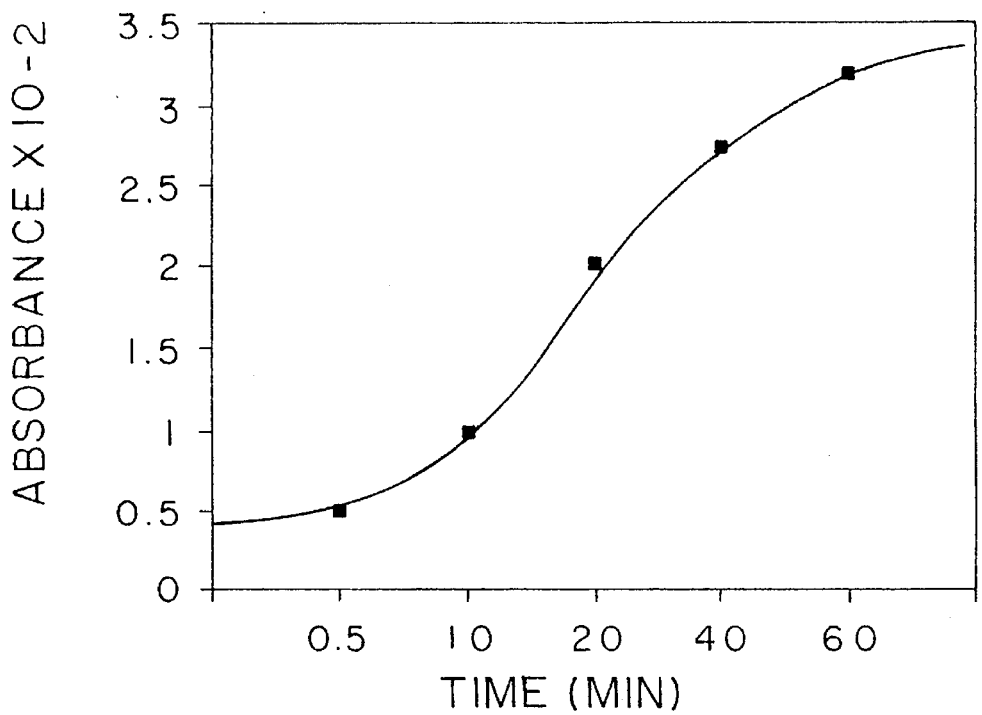
FIG. 6 shows a curve representing the formation of BSA-anti-BSA complex at the surface of the waveguide.

The waveguide was then immersed in a solution of anti-BSA (2 mg/ml) in phosphate buffer (0.01M, pH 7.4), and the binding of anti-BSA to BSA at the surface of the waveguide was monitored by the growth of the amide II band of anti-BSA (1560 cm$^{-1}$) in the ATR spectrum. A plot of the intensity of the amide II band of anti-BSA versus time exhibited a positive slope up to t=25 min and then reached a plateau (FIG. 6). This behaviour is indicative of binding of anti-BSA to BSA until equilibrium is reached and demonstrates that antibody-antigen complex formation at the surface of the waveguide can be monitored by this method, thus establishing its viability as the basis for an immunoassay.

EXAMPLE II

Synthesis of Labelled Antigens or Labelled Antibodies for Use in Homogeneous Interferometric Immunoassay

Synthesis of Anti-BSA-X(CO)$_3$

Anti-BSA (10 mg) was stirred for 16 h with HOOCC$_6$H$_5$Cr(CO)$_3$ (100 mg) in 20 ml of phosphate buffer in the presence of WSC (100 mg) at 4° C. The solution was dialysed (molecular weight cutoff 20,000) twice against phosphate buffer and once against water, and the dialysate was evaporated under reduced pressure to yield a yellow solid, anti-BSA-[Lys-$\epsilon$-NHCOC$_6$H$_5$Cr(CO)$_3$]$_{n'}$ henceforth denoted as anti-BSA-X(CO)$_3$. IR (in KBr): $\nu$(CO) 1975, 1910 cm$^{-1}$.

Synthesis of protein A-X(CO)$_3$

Protein A-[Lys-$\epsilon$-NHCOC$_6$H$_5$Cr(CO)$_3$]$_{n'}$ henceforth denoted as Protein A-X(CO)$_3$, was synthesized by the above procedure. IR (in KBr): $\nu$(CO) 1960, 1900 cm$^{-1}$.

Synthesis of BSA-X(CO)$_3$

BSA-[Lys-$\epsilon$-NHCOC$_6$H$_5$Cr(CO)$_3$]$_{n'}$ henceforth denoted as BSA-X(CO)$_3$, was synthesized by the above procedure. IR (in KBr): $\nu$(CO) 1969, 1900 cm$^{-1}$.

Synthesis of BSA-Z(CO)$_6$

To 10 ml of an aqueous solution of BSA (10 mg/ml), HOOCCCHCo$_2$(CO)$_6$ (100 mg) and WSC (100 mg) were added. The reaction mixture was stirred for 16 h at 4° C. and was then dialysed against distilled water twice. The dialysate was evaporated under reduced pressure at room temperature to yield a pale reddish-brown solid, BSA-[Lys-$\epsilon$-NHCOCCCHCo$_2$(CO)$_6$]$_{n'}$, henceforth denoted as BSA-Z(CO)$_6$. IR (in KBr): $\nu$(CO) 2096, 2057, 2023 cm$^{-1}$.

EXAMPLE III

Monitoring of Antigen-Antibody Complex Formation in Real Time

Figure 7:
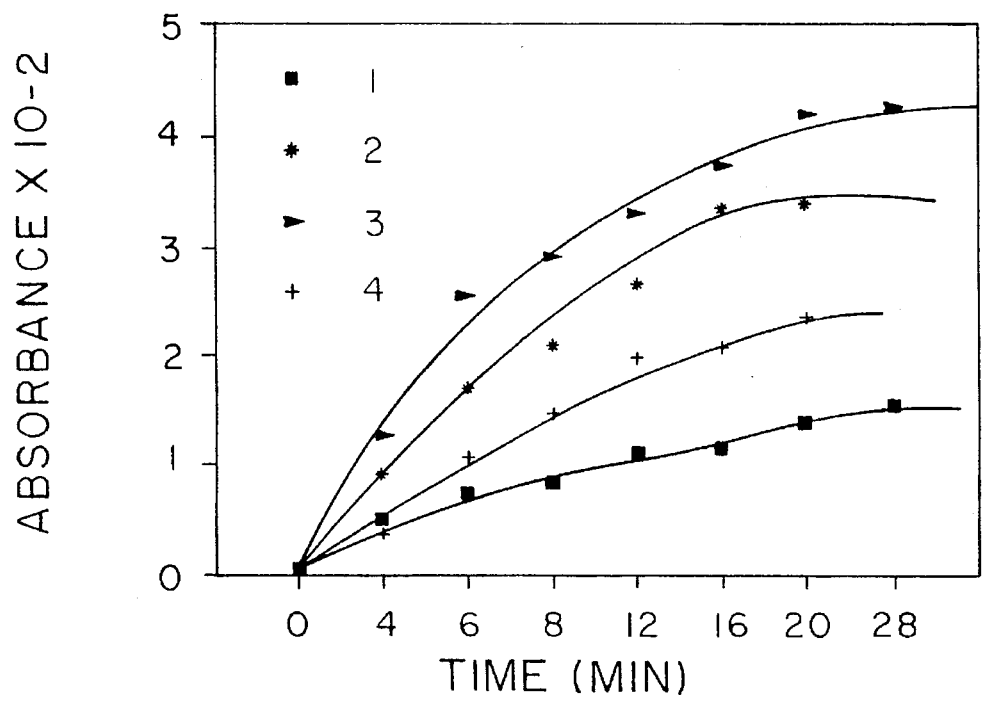
FIG. 7 shows 4 curves representing the variation in the extent of complex formation between BSA immobilized on a waveguide and anti-BSA-X(CO)$_3$ in the sample: (1) 0.05 mg/ml anti-BSA-X(CO)$_3$; (2) 0.1 mg/ml anti-BSA-X(CO)$_3$; (3) 0.15 mg/ml anti-BSA-X(CO)$_3$; (4) 0.19 mg/ml anti-BSA-X(CO)$_3$ and 0.25 g/ml free BSA.

A waveguide coated with CML to which BSA had been covalently bound was immersed in phosphate buffer (0.01M, pH 7.4). The ATR spectrum from the surface of the waveguide was recorded as the reference spectrum. The buffer was then decanted, and 4 ml of a buffer solution containing labelled anti-BSA-X(CO)$_3$ (0.05 mg/ml) was introduced. Spectral acquisition was commenced immediately upon addition of the antibody solution. The formation of the BSA-[anti-BSA-X(CO)$_3$] complex with time was monitored by the growth of the peaks in the ATR spectrum due to the $\nu$(CO) absorptions of the X(CO)$_3$ label (FIG. 7, curve 1). The solution was decanted, and the waveguide was washed 5 times with 15 mM HCl solution and 5 times with buffer solution. A new reference spectrum was recorded. The experiment was then repeated twice using solutions containing anti-BSA-X(CO)$_3$ at concentrations of (1) 0.1 mg/ml (FIG. 7, curve 2) and (2) 0.15 mg/ml (FIG. 7, curve 3). In a separate experiment, BSA (0.25 mg/ml) was added in solution together with anti-BSA-X(CO)$_3$ (0.19 mg/ml) to compete against BSA bound at the surface of the waveguide for the anti-BSA-X(CO)$_3$ binding sites (FIG. 7, curve 4). The variation in the intensities measured in the ATR spectrum as a function of the concentration of anti-BSA-X(CO)$_3$ in the solution (FIG. 7, curves 1–3) demonstrates that the signal recorded from the surface of the waveguide is proportional to the concentration of the labelled antibody in the assay medium. Furthermore, the decrease in the measured intensities upon addition of BSA in solution to compete against BSA bound at the surface of the waveguide for the binding sites of anti-BSA-X(CO)$_3$ (FIG. 7, curve 4) demonstrates the viability of the described technique as the basis for a homogeneous immunoassay.

EXAMPLE IV

A control experiment was carried out to evaluate the level of background signal in the ATR spectra, i.e. the contribution to the measured intensities of the absorptions of the X(CO)$_3$ label from anti-BSA-X(CO)$_3$ not bound to the BSA on the surface of the waveguide. The background signal can arise in two ways: (1) penetration of the evanescent wave beyond the bound fraction into the solution surrounding the waveguide, and (2) nonspecific binding of anti-BSA-X(CO)$_3$ on the surface of the waveguide. In this experiment, the bare waveguide was immersed in a phosphate buffer solution containing anti-BSA-X(CO)$_3$ (0.3 mg/ml). The ATR spectrum from the surface of the waveguide was recorded and compared to that obtained under the same conditions with the BSA/CML-coated waveguide (FIG. 8). The comparison indicates that the maximum contribution from anti-BSA-X(CO)$_3$ not specifically bound at the waveguide to the measured intensities of the X(CO)$_3$ absorptions in the latter spectrum is about 20%. Thus, the measured intensities stem predominantly from BSA-[anti-BSA-X(CO)$_3$] bound at the waveguide surface.

EXAMPLE V

In order to demonstrate that multiple antigens can be determined simultaneously in interferometric immunoassay, BSA was complexed to two different labels having distinct absorptions. A phosphate buffer solution containing BSA-X(CO)$_3$ and BSA-Z(CO)$_6$ was deposited onto the surface of an anti-BSA/CML-coated waveguide. In the ATR spectrum recorded from the surface (FIG. 9), the absorptions of the X(CO)$_3$ and Z(CO)$_6$ labels can be distinguished and their intensities measured independently. Thus, if these labels are complexed to different antigens (or antibodies), the quantitative determination of the two antigens (or antibodies) can be achieved in a single homogeneous immunoassay.

EXAMPLE VI

Simultaneous Determination of Multiple Infrared Markers in Solution from a Single FTIR Spectrum Solutions in toluene of three infrared markers, denoted X(CO)$_3$, Y(CO)$_3$ and Z(CO)$_{10}$ were prepared with randomly varying concentrations of the three markers. The FTIR spectra of the various solutions were recorded and are shown in FIG. 10. Although there was some significant overlap between the peaks of the different markers in these spectra, an accurate calibrated model for the analysis of all three components was developed employing the partial least square (PLS) algorithm; this model was able to predict the concentrations of each component within 0.01%. The simultaneous analysis of these components is possible because of the sharp band widths of infrared absorption bands, with each marker giving rise to at least two absorption bands in the region of the spectrum examined. The calibration set developed was employed to determine the concentration of antigens labelled with these markers deposited on the surface of an optical waveguide, demonstrating that multiple analytes can be quantitatively determined at the surface of the waveguide with the use of the infrared markers.

EXAMPLE VII

Simultaneous Monitoring Binding of Two Antibodies to Antigens Coated on the Surface of an Optical Waveguide Tobramycin-BSA (Tobra-BSA) and gentamicin-BSA (Genta-BSA) conjugates (1 mg/ml in PBS, pH 7.2) were adsorbed onto a ZnSe waveguide. The waveguide was washed 3 times with buffer. Anti-tobramycin and anti-gentamycin were adsorbed separately onto latex particles embedded with different infrared markers, denoted L-X(CO)$_3$ and L-Y(CO)$_3$. The embedded particles were obtained from Seradyn Corporation. A solution containing anti-Tobra-L-(CO)$_3$ and anti-genta-L-Y(CO)$_3$ in PBS buffer was placed on the surface of the coated waveguide, and subsequently an FTIR spectrum was recorded every 30 seconds. The binding of anti-Tobra-L-X(CO)$_3$ and anti-genta-L-Y(CO)$_3$ to the antigens on the surface of the waveguide was monitored by recording simultaneously the increase in the signals from each of the two labels in the FTIR spectra. The results shown in FIG. 11 indicate that the binding of two different antibodies at the surface of a single waveguide can be monitored simultaneously by labelling the antibodies with different markers that are distinguishable in the FTIR spectrum, thus demonstrating the feasibility of performing multiple analyte determination in a single immunoassay test. Control experiments to determine the background signal arising from penetration of the evanescent wave beyond the bound fraction into the sample and from nonspecific binding demonstrated that the signal from the labelled antibodies at the surface of the waveguide in the absence of the antigens was on the order of 10% of the maximum signal measured in their presence.

It should be understood that this detailed description, while indicating preferred embodiments of the invention, is given by way of illustration only, since various changes and modifications within the spirit and scope of the invention will become apparent to those skilled in the art.

What is claimed is:

1. A homogeneous immunoassay system for the simultaneous determination of the concentration of n different antigens in an aqueous sample, wherein n=2, which system comprises:

an interferometric signal emitted from an infrared source;

a waveguide through which said interferometric signal is propagated by internal reflection, said waveguide coated with n different antibodies and having at least one region thereof for immersion in an aqueous sample, the aqueous sample having corresponding antigens to each of the n different antibodies therein, each of the corresponding antigens having a labelled fraction and an unlabeled fraction, the labels of each corresponding antigen being different from one another and independently distinguishable from one another in the infrared spectrum, whereby the corresponding antigens can be complexed to their corresponding antibodies on the surface of the waveguide;

a detector for measuring the interferometric signal after its propagation through the waveguide; and a measuring device for taking a Fourier transform of the interferometric signal for determining an attenuation of the interferometric signal at wavelengths corresponding to an infrared absorption characteristic of said different and independently distinguishable labels incorporated into antigen-antibody complexes, thereby simultaneously determining the concentration of the n different antigens in the aqueous sample.

2. The homogeneous immunoassay system according to claim 1, wherein the waveguide is a rod.

3. The homogeneous immunoassay system according to claim 2, wherein the rod is made of a material selected from the group consisting of zinc selenide, germanium, AMTIR, silicon, zirconium fluoride or any other suitable infrared transmitting material of appropriate refractive index for multiple internal refraction.

4. The homogeneous immunoassay system according to claim 1, wherein the waveguide is an optical fiber.

5. The homogeneous immunoassay system according to claim 4, wherein the optical fiber is made of a material selected from the group consisting of zirconium fluoride, a chalcogenide or any other suitable infrared transmitting material of appropriate refractive index for multiple internal refraction.

6. The immunoassay system according to claim 1, wherein the waveguide is a slide.

7. The homogeneous immunoassay system according to claim 6, wherein the slide is made of a material selected from the group consisting of zinc selenide, germanium, AMTIR, silicon, zirconium fluoride or any other suitable infrared transmitting material of appropriate refractive index for multiple internal refraction.

8. The homogeneous immunoassay system according to claim 1, wherein the surface of the waveguide is coated with carboxy-modified latex.

9. A homogeneous immunoassay method for determining the concentration of n different antigens in an aqueous sample, the method using the system as defined in claim 1, comprising the steps of:

a) introducing antigens corresponding to the n antibodies to the waveguide, a known amount of the corresponding antigens labelled with an infrared marker, the markers of each corresponding antigen being different from one another and independently distinguishable from one another in the infrared spectrum;

b) monitoring the formation of antibody-antigen complexes at the surface of the waveguide; and c) determinating the concentration of each of the n different antigens as a function of said monitoring step.

10. A homogeneous immunoassay method according to claim 9, wherein the waveguide is selected from the group consisting of a rod, a slide and an optical fiber.

11. A homogeneous immunoassay method according to claim 9, wherein the surface of the waveguide is coated with carboxy-modified latex.

12. The homogeneous immunoassay system of claim 1, wherein n=3.

13. A homogeneous immunoassay system for the simultaneous determination of the concentration of n different antibodies in an aqueous sample, wherein n≧2, which system comprises:

an interferometric signal emitted from an infrared source;

a waveguide through which said interferometric signal is propagated by internal reflection, said waveguide coated with n different antigens and having at least one region thereof for immersion in an aqueous sample, the aqueous sample having corresponding antibodies to each of the n different antigens therein, each of the corresponding antibodies having a labelled fraction and an unlabeled fraction, the labels of each corresponding antibody being different from one another and independently distinguishable from one another in the infrared spectrum, whereby the corresponding antibodies can be complexed to their corresponding antigens on the surface of the waveguide;

a detector for measuring the interferometric signal after its propagation through the waveguide; and a measuring device for taking a Fourier transform of the interferometric signal for determining an attenuation of the interferometric signal at wavelengths corresponding to an infrared absorption characteristic of said different and independently distinguishable labels incorporated into antigen-antibody complexes, thereby simultaneously determining the concentration of the n different antibodies in the aqueous sample.

14. The homogeneous immunoassay system of claim 13, wherein n=3.

15. A homogeneous immunoassay method for determining the concentration of n different antibodies in an aqueous sample, the method using the system as defined in claim 13, comprising the steps of:

a) introducing antibodies corresponding to the n antigens to the waveguide, a known amount of the corresponding antibodies labelled with an infrared marker, the markers of each corresponding antibody being different from one another and independently distinguishable from one another in the infrared spectrum;

b) monitoring the formation of antibody-antigen complexes at the surface of the waveguide and c) determinating the concentration of each of the n different antigens as a function of said monitoring step.

* * * * *